US008017367B2

(12) United States Patent
Vassanelli et al.

(10) Patent No.: US 8,017,367 B2
(45) Date of Patent: Sep. 13, 2011

(54) BIOCHIP ELECTROPORATOR AND ITS USE IN MULTI-SITE, SINGLE-CELL ELECTROPORATION

(75) Inventors: Stefano Vassanelli, Padua (IT); Giorgio Cellere, Vicenza (IT)

(73) Assignee: Narvalus S.R.L. (IT)

( * ) Notice: Subject to any disclaimer, the term of this patent is extended or adjusted under 35 U.S.C. 154(b) by 1110 days.

(21) Appl. No.: 10/587,681

(22) PCT Filed: Jan. 29, 2004

(86) PCT No.: PCT/EP2004/000789
§ 371 (c)(1),
(2), (4) Date: Jul. 29, 2006

(87) PCT Pub. No.: WO2005/075656
PCT Pub. Date: Aug. 18, 2005

(65) Prior Publication Data
US 2007/0155015 A1    Jul. 5, 2007

(51) Int. Cl.
*C12N 13/00* (2006.01)
*C12M 1/42* (2006.01)
*C12M 3/00* (2006.01)
*C12M 1/00* (2006.01)

(52) U.S. Cl. .......... 435/173.6; 435/285.2; 435/173.4; 435/173.1; 435/173.5; 435/461; 435/470; 435/288.4; 435/288.3; 435/305.3; 435/305.2; 435/30; 435/288.2; 204/403.01

(58) Field of Classification Search ............ 435/285.2, 435/173.4, 173.6, 173.1, 173.5, 461, 470, 435/288.4, 288.3, 305.3, 305.2, 30, 288.2; 204/403.01
See application file for complete search history.

(56) References Cited

U.S. PATENT DOCUMENTS

| | | | | |
|---|---|---|---|---|
| 5,134,070 A * | 7/1992 | Casnig | ...................... | 435/173.6 |
| 6,132,683 A * | 10/2000 | Sugihara et al. | ........... | 422/82.01 |
| 6,300,108 B1 | 10/2001 | Rubinsky et al. | .......... | 435/173.6 |
| 6,352,535 B1 * | 3/2002 | Lewis et al. | ..................... | 606/45 |
| 6,368,851 B1 * | 4/2002 | Baumann et al. | ......... | 435/285.2 |
| 7,521,224 B2 * | 4/2009 | Johnson et al. | ............ | 435/285.2 |
| 2002/0090649 A1 * | 7/2002 | Chan et al. | ..................... | 435/7.1 |
| 2003/0157587 A1 * | 8/2003 | Gomez et al. | ................... | 435/30 |
| 2005/0112544 A1 * | 5/2005 | Xu et al. | ......................... | 435/4 |

FOREIGN PATENT DOCUMENTS

WO    WO 02/31171    4/2002

OTHER PUBLICATIONS

Lin, Y-C. et al.; A Microchip for Elecroporation of Primary Endothelial Cells; Sensors and Actuators A, Elsevier Sequoia S.A., Lausanne, Switzerland, vol. 108, No. 103, pp. 12-19 (Nov. 15, 2003).

(Continued)

*Primary Examiner* — Nathan A Bowers
(74) *Attorney, Agent, or Firm* — Lorusso & Associates

(57) ABSTRACT

The introduction of genetic material or molecules of biological interest into cells is a procedure with an increasing interest both for experimental and application purposes, so that electroporation is a widely used technique, but the electroporation of single adhering cells is still impaired.

The present application describes an apparatus for the electroporation of any kind of cell adhering to a substrate at any stage of development, where an electrical signal can be driven and applied to a single adhering cell in culture in order to obtain its electroporation. The method to electroporate a single adhering cell with the apparatus of the invention is also described.

12 Claims, 8 Drawing Sheets

OTHER PUBLICATIONS

Huang, Y. et al., Microfabricated electroporation Chip for Single Cell Membrane Permeabilization, Sensors and Actuators A, Elsevier Sequoia S.A., Lausanne, Switzerland, vol. 89, No. 3, pp. 242-249 (Apr. 15, 2001).

Huang, Y. et al., Flow-Through Micro-Electroporation Chip for High Efficiency Single-Cell Genetic Manipulation, Sensors and Actuators A, Elsevier Sequoia S.A., Lausanne, Switzerland, vol. 104, No. 3, pp. 205-212 (May 15, 2003).

Lin, Y.-C. et al., Electroporation Microchips for Continuous Gene Transfection, Sensors and Actuators A, Elsevier Sequoia S.A., Lausanne, Switzerland, vol. 79, Nos. 2-3, pp. 137-143 (Oct. 15, 2001).

Olfsson, J. et al., Single-Cell Electroporation, Current Opinion in Biotechnology, vol. 14, No. 1, pp. 29-34 (Feb. 1, 2003).

* cited by examiner

BIOCHIP ELECTROPORATOR AND ITS USE IN MULTI-SITE, SINGLE-CELL ELECTROPORATION

FIELD OF THE INVENTION

This invention refers to a method and apparatus for the individual electroporation of any kind of cell adhering to a substrate at any stage of development.

STATE OF THE ART

Electroporation is a widely used technique employed to introduce genetic material or molecules of biological interest into cells. Application of an electrical signal to the cell produces the opening of pores in the membrane, allowing the molecules in the extracellular solution to enter the cell.

Several electroporation techniques have been established. They can be divided in two classes:
(i) techniques for the electroporation of a population of cells
(ii) techniques for the electroporation of single cells.
Electroporation of a Population of Cells.

The electroporation of a population of cells in suspension, which is the most used and representative of the first class, is routinely performed after the cells have been removed from the culture substrate, by using enzymes such as trypsine. Then, cells are suspended in electroporation medium and high voltages (up to 1000V and more) are applied between two large metal electrodes, typically spaced 2 or 4 mm. The cells suspension is then transferred into a suitable culture chamber, where cells are free to settle down and adhere onto the bottom substrate where they are cultured.

This technique implies several drawbacks.

The actual voltage drop across each cell can not be controlled. Many cells close to the electrodes die during the high voltage application, others are electroporated to different extent depending on their position within the electric field between the electrodes and on the local variations of the applied electrical field that is not uniform.

The method can only be applied to a large population of cells.

Cells must be detached from the adhesion substrate, thus cells are stressed and damaged in the process.

Electroporation of Single Cells.

A technique for single cell electroporation has been developed by Rubinsky et al. and described in the U.S. Pat. No. 6,300,108.

This technique employs a cell sized electroporation chamber integrated into a silicon microchip. The cell, is first introduced in the chamber and placed onto an opening in a silicon substrate, then it is electroporated and made permeable to genetic constructs.

The above technique has some drawbacks:

The system set-up is complex, moreover, the integration of a large array of "single cell electroporators" into a microchip has not been accomplished yet and would be very expensive even with state of the art technology.

The cell membrane cannot adhere extensively to the substrate and therefore growth and development are impossible for all cell types requiring adhesion (which is the case for most type of cells);

The cell has to be placed into a microchamber; this is a difficult procedure and far away from the protocols routinely used for cell culture.

From the above it is clear the need of an electroporation apparatus allowing to overcome the above said drawbacks.

SUMMARY

The Applicant has now found an apparatus for individual electroporation of any kind of cell adhering to a substrate in order to solve all the drawbacks above mentioned.

Therefore, it is an object of the present invention an apparatus for electroporation comprising a wave generator, a biochip containing an array of microelectrodes and a control system that permits to transfer the signal to a pre-selected single microelectrode of the biochip.

It is a further object of the present invention the biochip comprising an array of microelectrodes comprised on a suitable insulating layer mounted on a solid substrate; means to electrically connect said microelectrodes to a switching system; a cell culture chamber where the cells can be grown and adhere in contact with said array of microelectrodes on a surface formed by said insulating layer containing said array of microelectrodes on said solid substrate.

Further objects of the invention are the methods for cell electoporation using said apparatus, this methods further performing electroporation to at least a single adhering cell and electroporated cells obtained with the same.

These and other objects as well as features and advantages of the present invention will be better understood from the detailed description set forth below.

DETAILED DESCRIPTION OF THE INVENTION

The features of the invention will become apparent in the course of the following description and from the preferred embodiments which are given for illustration and have no limiting purposes.

The present invention allows to overcome the drawbacks of existing techniques through an apparatus comprising an electrical waveform generator, a biochip comprising an array of microelectrodes and a control system that permits to transfer the signal to a pre-selected single microelectrode of the biochip.

Preferably the control system consists of a personal computer, equipped with a software program, capable of designing various waveform signals within the wave generator and selecting the microelectrodes by the use of a switching system.

Figure 1:
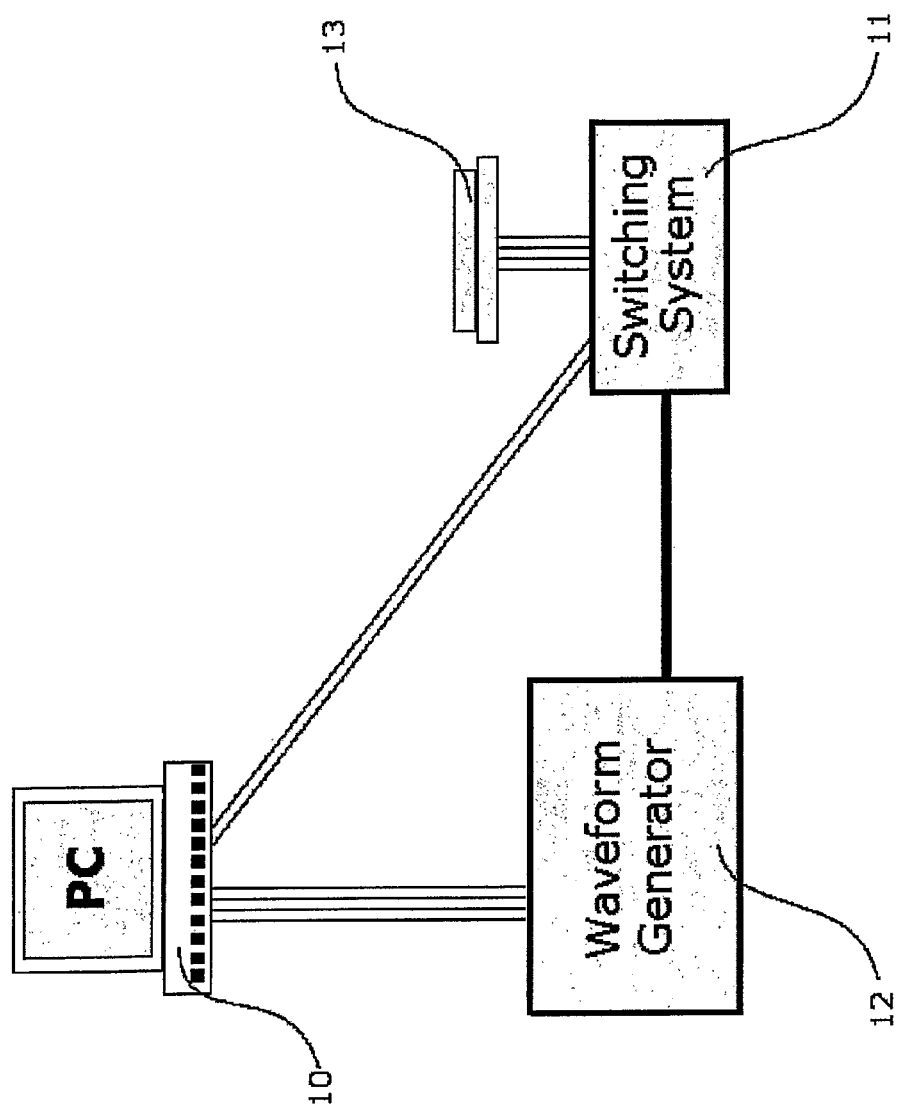
FIG. 1 shows a schematic representation of the apparatus

The apparatus according to the present invention is schematically represented in FIG. 1 wherein a personal computer 10, a switching system 11, a signal generator 12 and a biochip 13 are displayed.

The personal computer 10 is equipped with a software program allowing the operator to fully control the electroporation process, programming the shape and the timing of the waveform of the signal to be delivered to the biochip.

The electrical waveform generator 12 used in the apparatus according to the present invention is a common device, readily available on the market; the switching system 11 can easily be designed and implemented by the man skilled in the art.

The biochip 13, comprising an array of microelectrodes, a suitable insulating layer, where said insulating layer is on a solid substrate, means to electrically connect said microelectrodes to a switching system, a cell culture chamber where the cells can be grown in contact with said array of microelectrodes and adhere on the surface formed by said insulating layer containing said array of microelectrodes on a solid substrate, is described hereinafter in detail according to its preferred embodiments.

The lay-out of the biochip according to the present invention is displayed in FIGS. 2a and 2b as one preferred embodiment and will be described with reference to both figures, wherein the reference numbers designate identical or corresponding parts throughout the two views.

Figure 2:
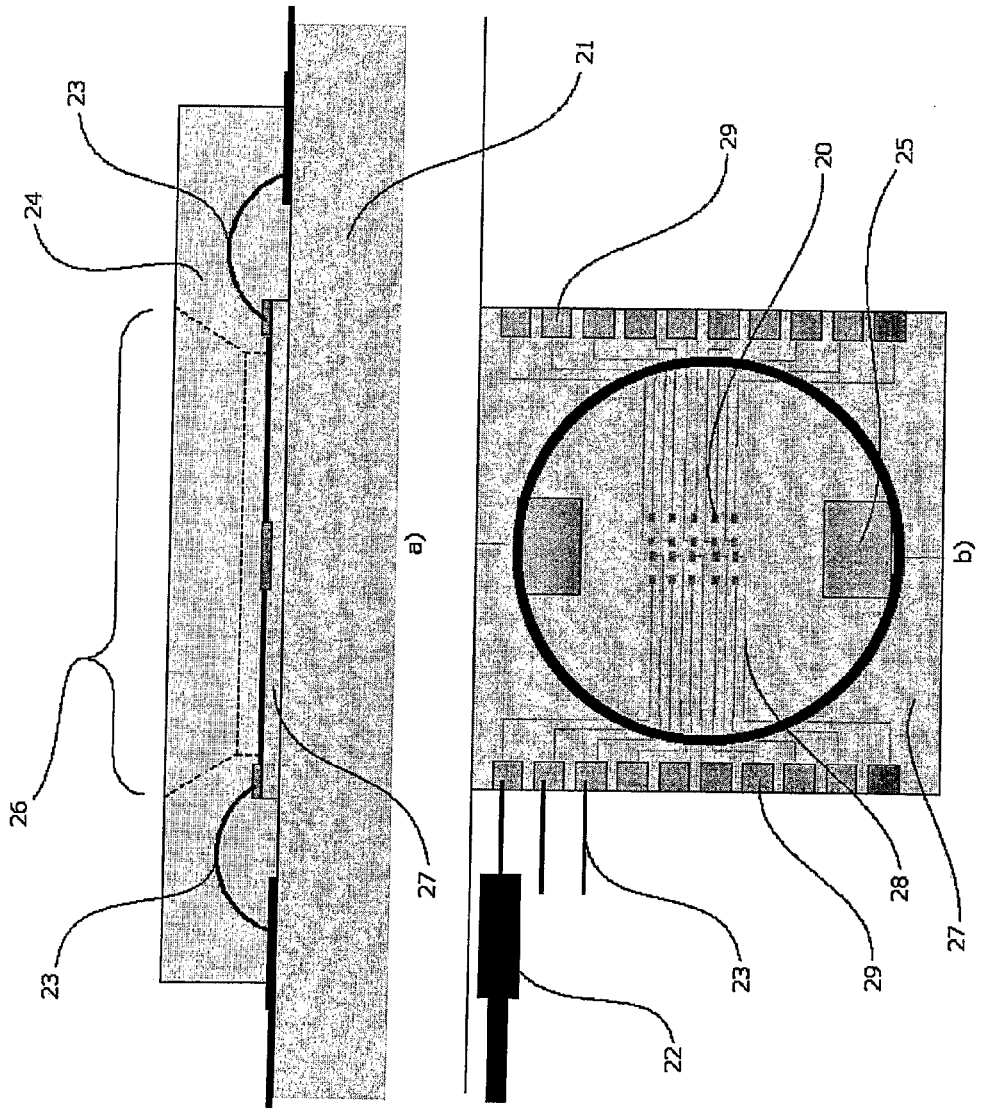
FIG. 2 shows a biochip according to the invention; top view (FIG. 2b) and cross section (FIG. 2a)

In the FIG. 2a said biochip is displayed mounted on a dielectric support 21 mounting, in turn, a cell culture chamber 24 with an opening 26 placed in the centre, the base surface of which is formed by an insulating layer, comprising an array of microelectrodes of a size comparable to the cell to be electroporated, on a solid substrate 27. Said array of microelectrodes 20 being integrated on an insulating layer mounted on a solid substrate 27 on which is placed a cell culture chamber 24 provided with an opening 26, the bottom of said opening 26 is the top surface of the biochip 13 where the cells are grown adhering on and in contact with said array of microelectrodes. Said array of microelectrodes are electrically connected via conductive traces 28 to conductive pads 29 electrically connected, in turn, to a couple of external parallel connectors 22 through wire bonding 23 covered by the outer portion of the cell culture chamber 24 encircling the opening 26.

The biochip 13 is electrically connected to the switching system 11, as displayed in FIG. 1, through appropriate means of connection such as a cable plugged in the connectors 22.

In a preferred embodiment of the present invention, the dielectric support 21 is made of vetronite. Other equivalent materials such as glass or ceramic are not excluded.

In a preferred embodiment of the present invention the solid substrate of the biochip 13 consists of a semiconductor substrate, such as for example a silicon substrate, of a suitable form, such as, for example, of square form, having suitable lateral dimension, preferably of about ten millimeters and covered with an insulating layer preferably of $SiO_2$. Silicon is not the only possible substrate for such a device: for example, glass or other transparent substrates can be used as well. However, silicon has the advantage of well consolidated and repeatable manufacturing techniques derived from the microelectronics industry, allowing precise control of each device parameter.

In any case transparent substrates can be preferred, allowing the use of inverted microscopes for cell observation.

Two electrodes of large dimensions 25 (around 1 square mm), integrated in the solid substrate covered with an insulating layer 27, act as ground reference. In alternative it is possible to, have the said electrodes acting as cold terminal for the electroporation electrical current and a wire, made of Ag/AgCl, as ground potential reference.

In the array of microelectrodes 20 of a size comparable to the cell to be electroporated and comprised in an insulating layer covering a solid substrate, each microelectrode can be driven individually and separately from the others thanks to their individual connections to the switching system 11, thus allowing very precise and punctual control of the electroporation process. Microelectrodes employed can be of conductive or capacitive type.

FIG. 2b shows (not in scale) the layout of twenty microelectrodes 20, each one with an active area (that is the area delivering the signal to the cell) of twenty μm long by twenty μm wide. This layout provides a relatively good balance between the number of stimulating sites, the microelectrodes, and the interconnections between microelectrodes and of the biochip required for the external supplying of the microelectrodes. Higher number and density of microelectrodes can be achieved, depending on the type of cell to be electroporated.

In order to favour cell adhesion on the biochip, the surface of said opening 26 of the biochip cell culture chamber 24 is covered with adhesion molecules (for example poly-L-lysine) before starting cell culture. Many different adhesion molecules can be used for coating the substrate allowing good cell adhesion with a distance of a few tens of nanometers between cell membrane and semiconductor substrate covered with an insulating layer 27 comprised in the opening 26 of the culture chamber.

Microelectrodes may be of different shape and dimensions as long as their size is comparable to cell size, normally they are planar or, in general, designed to allow a good adhesion of the cell membrane on their surface (normally at least ten percent of the total cell membrane has to be in contact with the electrode), their dimensions range from 1 μm to 50 μm. Said microelectrodes are made of bio-compatible conductive material capable to deliver the necessary current/voltage AC and/or DC signals to the cells.

Figure 3:
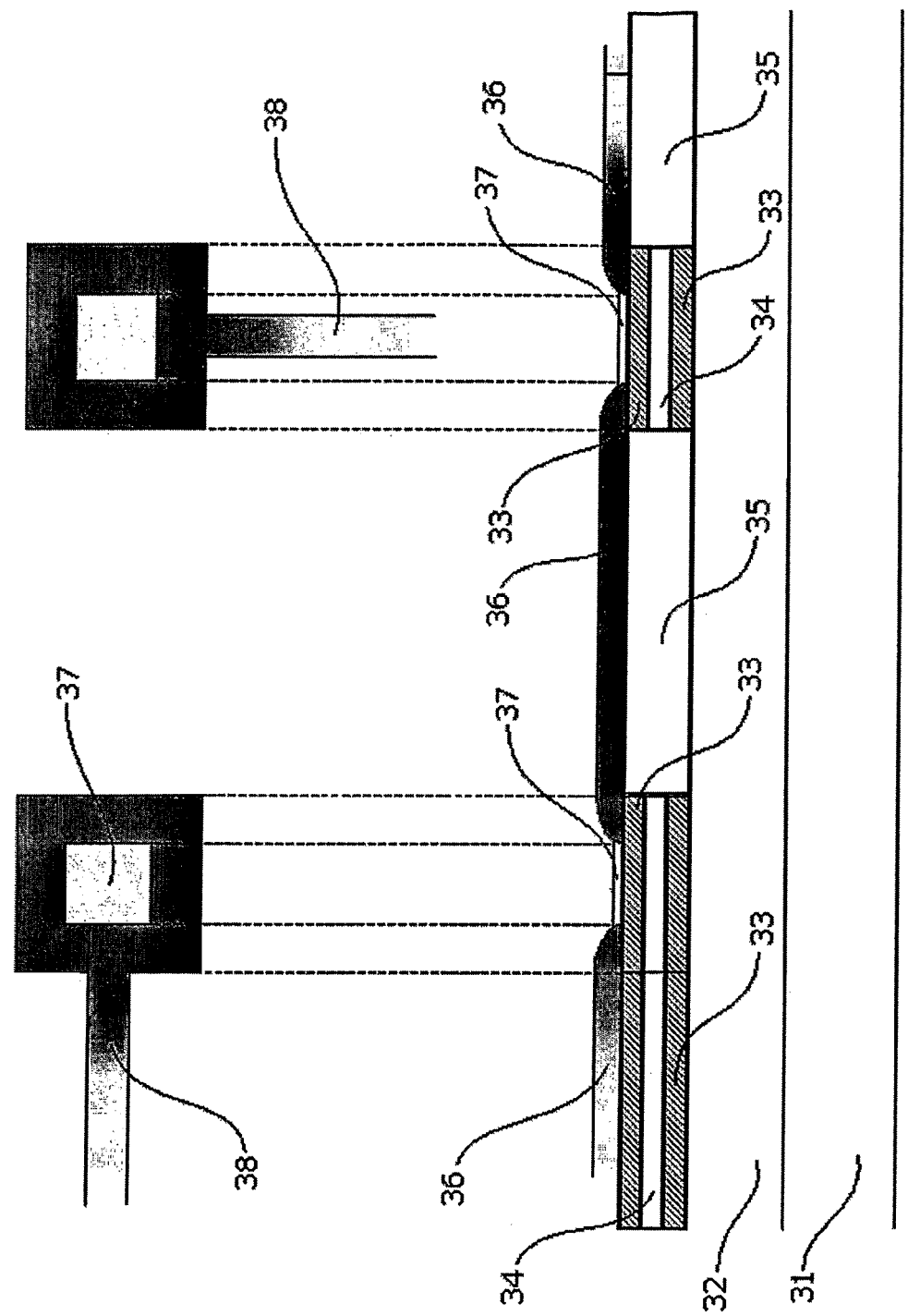
FIG. 3 shows a cross section of a conductive microelectrode according to the invention

Conductive microelectrodes are made of materials which can be chosen among several bio-compatible metals and alloys and can be single layer or a multilayer. A preferred embodiment of a conductive microelectrode used in the biochip of the apparatus according to the present invention is depicted in FIG. 3. Said microelectrodes are realised over a silicon substrate 31 covered with a $SiO_2$ insulating layer 32. Microelectrodes and their connecting traces 38 are made by a "sandwich" of two titanium nitride (TiN) layers 33 and an aluminium layer 34, covered with a gold layer 37. This solution has several advantages, combining the high thermal budget and biocompatibility of TiN to low electrical resistance of Al. Microelectrodes are separated by $SiO_2$ insulating layer 35. The part of the chip not to be directly exposed to the cells (comprising traces 38 connecting microelectrodes) is covered by a silicon nitride ($Si_3N_4$) layer 36, which leaves exposed the active part of the microelectrodes only. Different materials (such as $SiO_2$ or organic polymers) can be used for this purpose.

Figure 6:
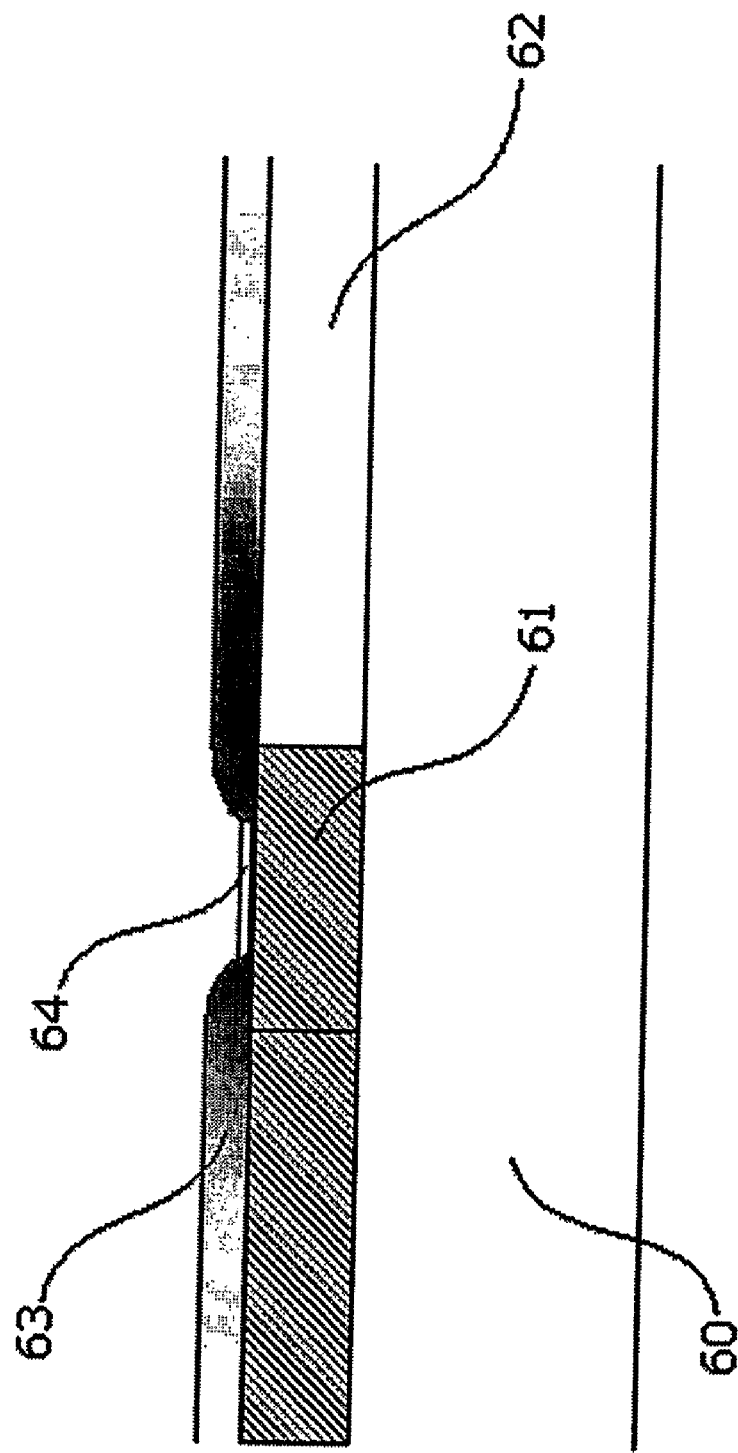
FIG. 6 shows a cross section of a capacitive microelectrode according to the invention
FIG. 7 and FIG. 8 display two particular waveforms of the electroporation driver signal. Parameters value, such as time and amplitude are given in the experiments descriptions

In another embodiment of the invention, microelectrodes of capacitive type are realised introducing a thin insulating material to cover the active part of the microelectrode itself. With reference to FIG. 6, microelectrodes are realised on an insulating substrate 60 by using a conductive layer 61 (that can be made of metal or semiconductor or the above mentioned sandwich of TiN/Al/TiN, or other equivalent materials and combination of materials) and a thin insulating layer 64 (typically thinner than 25 nm) which manages to electroporate the cell via a capacitive coupling. Microelectrodes are separated by insulating material 62 and covered in non exposed areas by a passivation layer 63.

According to a further embodiment of the microelectrodes of the biochip according to the present invention, said microelectrodes can be realised using Metal Oxide Semiconductor (MOS) technology in order to achieve a higher electrode density, and each of them can be addressed in a way similar to that of semiconductor memory cells.

Figure 4:
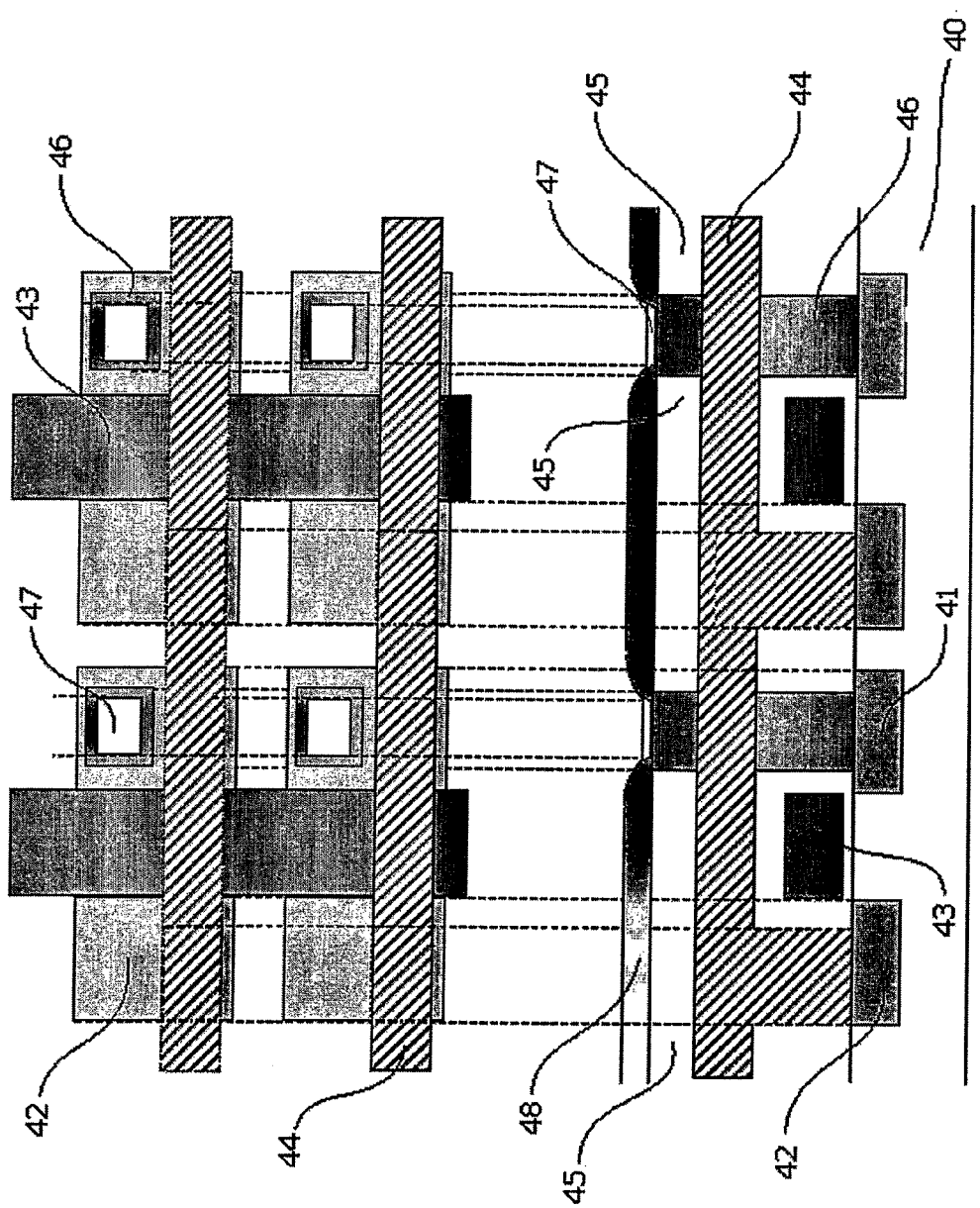
FIG. 4 shows top view and cross section of an array of MOSFET conductive microelectrode according to the invention

With reference to FIG. 4, an array of MOSFET (Metal Oxide Semiconductor Field Effect Transistor) is realised on the silicon substrate 40 with conventional microelectronic techniques, that is by implanting in a p-type substrate 40, two n-doped regions, 41 and 42, which constitute the drain and the source of the transistor, respectively. The gate 43 of these MOSFETs is realised in n+ doped polysilicon and is common to all devices in a row (word line). The drain 41 of all devices in a column are connected together by using a metal contact plug (normally realised in tungsten) and a metal line 44 (bit line). The metal is surrounded by isolation oxide 45. The source 42 of the transistor is connected via a metal (usually tungsten) plug 46 to a thin gold layer 47 which acts as the active microelectrode. Part of the chip not to be exposed can be covered with a passivation layer 48.

Inverting p-type regions with n-type regions and n doping with p doping it is possible to realise a pMOSFET instead of the nMOSFET described above with analogous results in terms of integration.

With this technology, the minimum distance between two microelectrodes can be as low as one micrometer thus allowing to reach and electroporate single cells with high spatial resolution.

Figure 5:
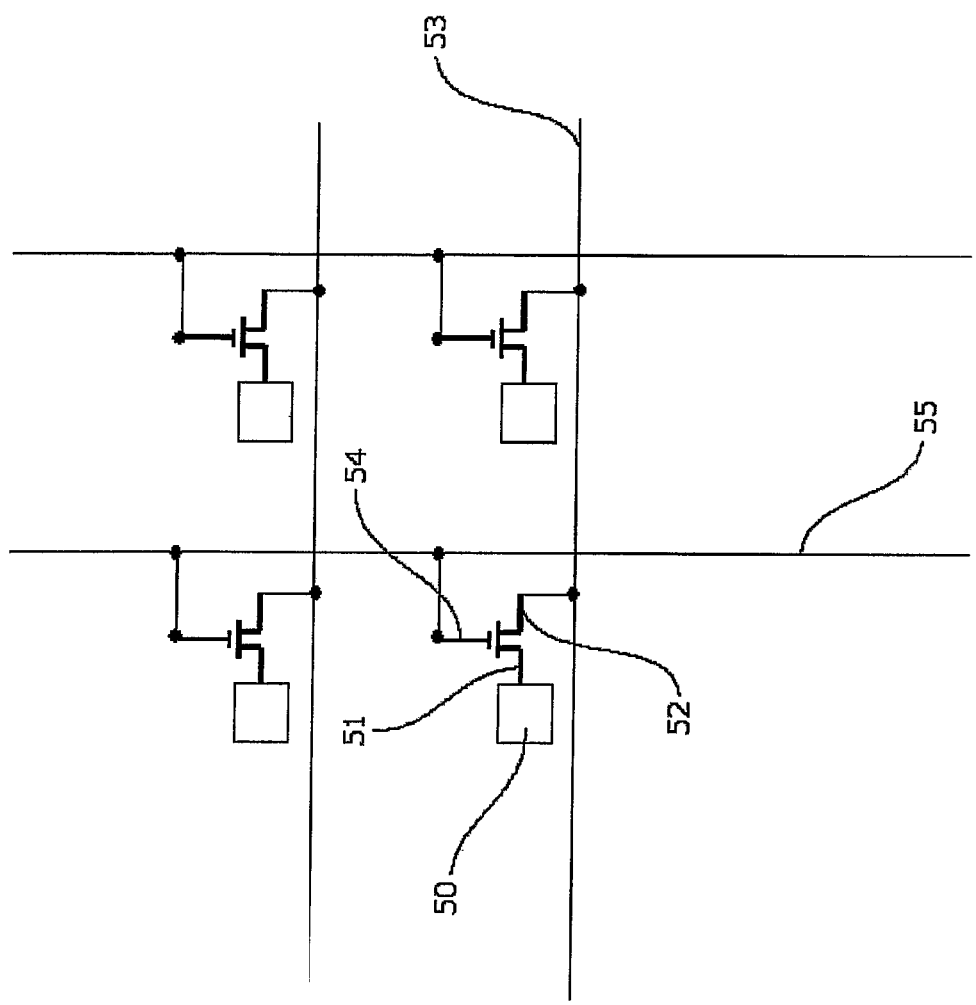
FIG. 5 shows a schematic representation of an array of MOSFET conductive microelectrode according to the invention

In FIG. 5 a schematic of an array of microelectrodes as described above is displayed. Microelectrodes 50 are connected to the sources 51 of MOSFETS, whose drains 52 are connected to word line 53 and gates 54 to bit lines 55. If the gate of a MOSFET is kept at a voltage $V_G$ higher than the threshold voltage $V_{TH}$, the drain is kept at $V_D$, and the source is left open, the voltage of the latter terminal is $V_D$-$V_{TH}$. This mechanism can be used to control the voltage of the microelectrode 50 connected to the source 51 of a selected MOSFET by controlling the voltages of the word line 53 and the bit line 55 which define its position in the array.

The electroporation apparatus according to the present invention does not require particular adhesion molecules and is independent from the procedures for cells plating, positioning and culturing as well.

The apparatus according to the present invention allows the performing of electroporation with the following advantages:
  electroporation on adhering cells
  electroporation onto a number of different single cells within the same culture
  electroporation timing arbitrarily chosen for each target cell,
  electroporation degree (i.e. pores number, size and duration) controlled for each target cell, by controlling the voltage developing across the membrane via the individual cell/microelectrode electrical coupling,
  electroporation in different sites of the same cell using different microelectrodes, in case of cells large enough to cover different microelectrodes.

Due to its features, the method according to the present invention is extremely useful for high throughput screening of molecules impermeable to the cell membrane. Drugs, genetic constructs and proteins can be tested individually on a number of single cells on the same microchip. Timing of delivery and combinations of different molecules can be set for each target cell.

The method according to the present invention can be employed in basic research (for example for screening of genes function) as well as in the phase of "discovery" of new drugs. A substantial increase of the experimental yield and a decrease of the experimental costs are expected. Due to the good efficiency and control of cell electroporation, it is not excluded that the technique will become useful even in the "production" phase of drugs from transfected cells and for gene therapy.

The method for electroporation achievable with the apparatus hereinbefore describe substantially comprises the following steps:
  cultivate cells since the adhering stage is reached
  add in the culture medium at least one compound to be electroporated in at least one single cell of the said cells
  selected at least one single cell and at least one microelectrode on which said selected single cell is adherent
  generate at least one electric signal suitable to electroporate said at least one single cell with said at least one compound to be electroporated and drive said electric signal to the said one microelectrode on which said selected single cell is adherent.

Hereinafter four experiments performed with the method using the apparatus according to the present invention are described in the following examples.

Example 1

Transfection of Cos-7 Cells with Oligonucleotides

The goal of the experiment was the transfection of individual target cells with double-stranded DNA oligonucleotides.

Oligonucleotides marked with a fluorescent label were used and their penetration into the target cell after electroporation was afterwards detected by the presence of intracellular fluorescence.

Cos-7 cells were maintained in culture using a conventional culture medium. After having been kept two days in culture, they were trypsinized, resuspended in culture medium and plated on the biochip cell culture chamber according to the present invention at a density of about 35,000 cells/cm$^2$ of chip surface. Before plating, the surface of the chip was washed carefully, rinsed, dried, and sterilised with UV light. The biochip was then coated with poly-L-lysine by adsorption from a 20 µg/ml aqueous solution for 2 h and dried. Cells were incubated at 37° C. and 5% $CO_2$.

Double-stranded DNA oligonucleotides of 87-113 pair bases and containing each one a residue labelled with a fluorescent dye (either NED or FAM) were then synthesised. The oligonucleotides were solubilized in water during the synthesis to a final concentration of about 40 ng/µl. Prior electroporation the oligonucleotides solution was diluted 1:1 in HBS 2×. After removing the culture medium, about 60 µl of the oligonucleotides solution were applied to the culture chamber just before electroporation.

Individual cells growing in contact with a single microelectrode were identified by microscopic observation. After selecting with the control system one of the microelectrodes in contact with a single cell, a suitable electroporation signal was delivered and the same operation was repeated for each target cell.

A wave form generator driven by a personal computer, generates the electrical signal that is delivered to the biochip according to the present invention. Said signal is send through a 50 Ω coaxial cable to the switching system that permits to transfer the signal to a pre-selected single electrode of the biochip according to the present invention. The external parallel connectors are connected to the biochip through a printed circuit. The reference ground is made by connecting the previous switch ground to an Ag/AgCl electrode dipped into the electrolyte solution where the cultured cells lie.

Figure 7:
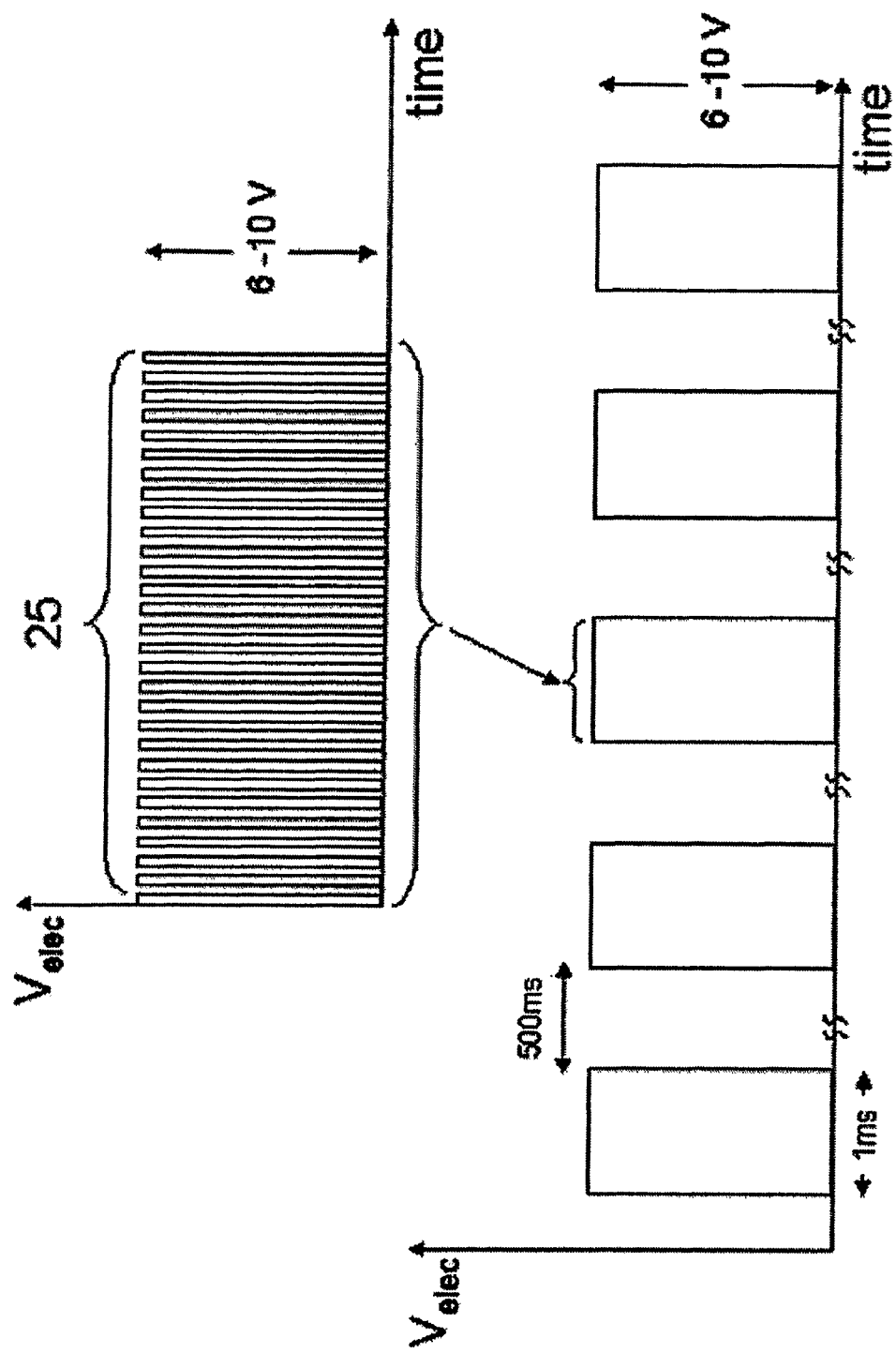

The waveform of the electroporation signal is depicted in FIG. 7. Five trains of 25 square pulses (1 ms duration, 10 μs rise/fall time) repeated at a time interval of 500 ms were found to be suitable for a successful transfection of Cos-7 cells.

After electroporation cells were washed with a standard physiological solution and observed with a fluorescence microscope. Successful transfection of each target cell was detected by the presence of cell fluorescence. Cell survival was monitored for 24 h after transfection by observation of the cell morphology.

About 80% of target cells were successfully transfected and a good percentage of cells survival (50-80%) was achieved with pulses of 6-10 V amplitude and 1-10 μs rise/fall time.

The degree of transfection, judging from the intensity of the intracellular fluorescence, was directly related to the amplitude and inversely related to the rise time. Contrary, cell survival was decreasing with the voltage amplitude and increasing with the rise time. The time interval between trains was critical: for a time interval larger than 500 ms, transfection did not occur. For a time interval smaller than 500 ms cell survival substantially decreased. As a best compromise in order to obtain the highest percentage of transfection and cell survival we routinely used pulses of 9 V and 10 μs rise time.

Example 2

Transfection of Cos-7 Cells with a DNA Plasmid Vector

In another experiment performed with the method according to the present invention the goal was the transfection of individual target cells with a DNA plasmid vector.

Individual Cos-7 target cells were transfected using the apparatus according to the present invention with a plasmid vector coding for the GFP (Green Fluorescent Protein). The synthesis of GFP in the cell cytoplasm was observed with a fluorescence microscope and was indicating successful transfection.

Transfection with plasmid vectors is a technique routinely used in many laboratories for the investigation of genes function.

The Cos-7 target cells were identical to the previous experiment.

A DNA plasmid vector of 5 kB containing the GFP coding gene was used. After amplification and purification the DNA was solubilized to 50 μg/ml in water. Prior electroporation the DNA solution was diluted 1:1 in HBS 2×. After removing the culture medium, about 60 μl of the DNA solution (25 μg/ml) were applied to the culture chamber just before electroporation.

Target cells were selected as in the previous experiment. The waveform of the electroporation signal used was identical to the previous experiment except that the number of pulses per train was elevated to 50. After 48 h the transfected target cell has undergone a replication cycle splitting in two cells expressing the GFP. The typical cytoplasmic pattern of GFP expression is visible in both cells. The two cells, because of replication and of intrinsic cell motility, have slightly moved away from the microelectrode which was originally covered by the mother cell alone.

Example 3

Electroporation of Rat Hippocampal Neurons with Fluoroscein

In a third experiment, the electroporation with the apparatus according to the invention of rat hippocampal neurons with fluoroscein was performed.

Neurons were dissociated from the hippocampi of Wistar rats at 18 d gestation (Banker and Cowan, 1977). They were preplated twice to get rid of glia cells and suspended in DMEM with glutamax I (no. 61965026, Gibco, Eggenstein, Germany) supplemented with 10% (vol) fetal bovine serum (10106078, Gibco) and 1% (vol) penicillin (15140114, Gibco) (Brewer et al., 1993; Vassanelli and Fromherz, 1998). The final concentration was 350,000 cells per milliliter.

The surface of the chip was wiped carefully with a 1% solution of a liquid dish detergent, rinsed with milli-Q water (Millipore, Bedford, Mass.), dried, and sterilized with UV light. The chips were coated with poly-L-lysine (molecular weight >300,000; Sigma, Heidelberg, Germany) by adsorption from a 20 μg/ml aqueous solution for 1 h and dried. We applied 350 μl of the cell suspension toculture chamber. Leibovitz L-15 medium (100 μl) with glutamax I (31415029, Gibco) supplemented with 5% fetal bovine serum were added. The density of cells was ~100,000 cm$^2$. The chips were kept at 37° C. and 10% $CO_2$ for 2 h. Then the medium was removed, and the cells were cultured in a serum-free medium (Brewer et al., 1993; Evans et al., 1998; Vassanelli and Fromherz, 1998) using 450 μl neurobasal medium (Gibco, 21103049) supplemented with 2% (vol) B27-medium (17504036, Gibco) and 1% (vol) glutamax I (35050038, Gibco) for 4-7 d. Electroporation was performed with neurons maintained for a minimum of 6 d to a maximum of 12 d in culture.

Figure 8:
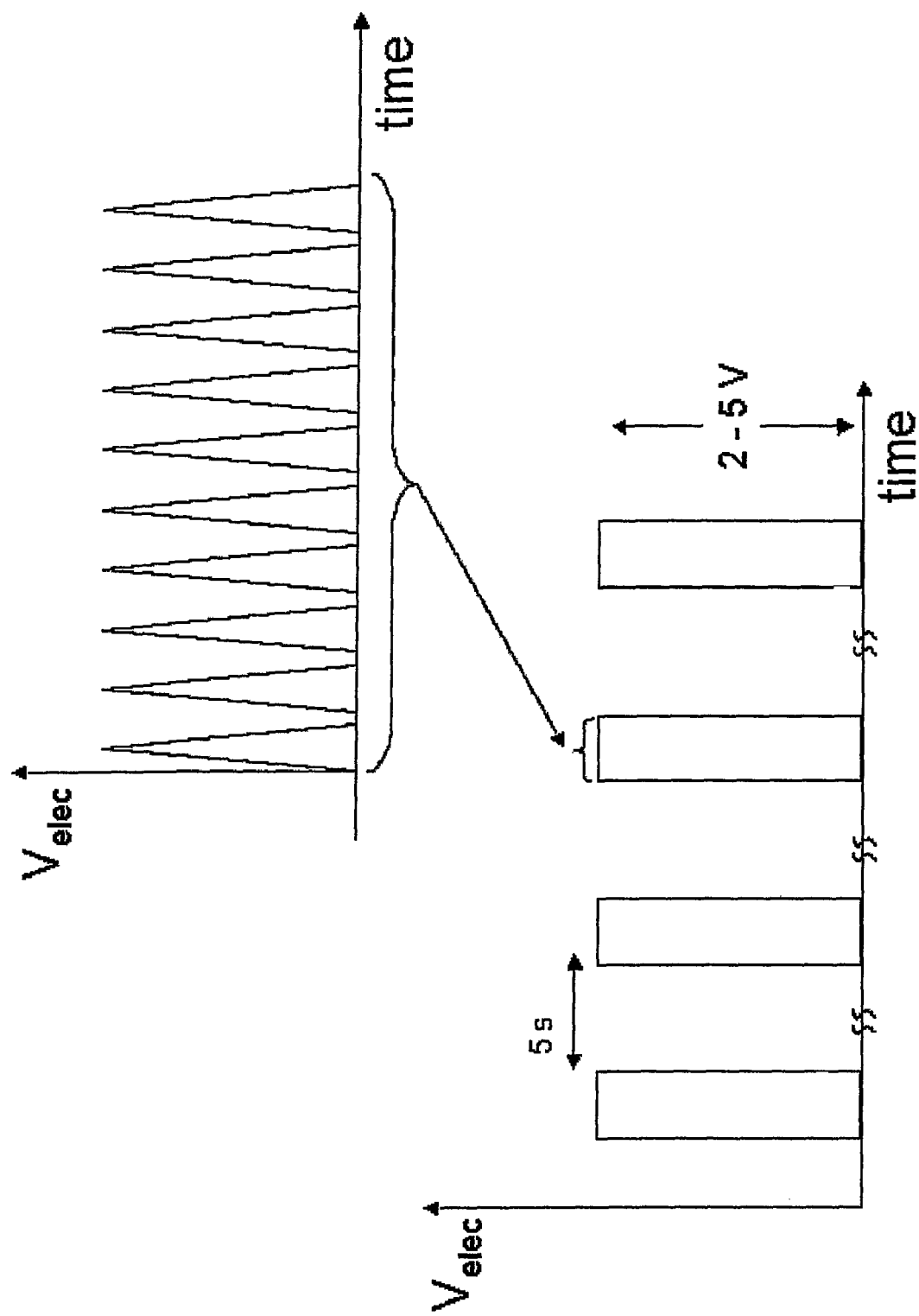

Fluorescein was solubilized in standard physiological solution (10 μM) and applied to the culture chamber just prior electroporation. After washing twice with physiological solution cells were observed under a fluorescence microscope. Electroporation of single rat hippocampal neurons was obtained by application to the microelectrode of trains of triangular voltages, each triangular waveform has amplitude equal to 4V and single triangular duration equal to 1 ms with rise time equal to fall time (FIG. 8).

It has to be noted that contrary to Cos-7 cells and numerous other cell lines, neurons are excitable cells and unwanted stimulation of their electrical activity during electroporation has to be limited. We reduced unwanted stimulation (i) by diminishing the number of pulses per train (10 pulses versus 25 or 50 used with Cos-7 cells), (ii) by increasing the interval between trains (5 s instead of 500 ms) and (iii) by use of triangular voltages.

Example 4

Electrophysiological Activity of Cell During Electroporation (Cos-7 and Rat Hippocampal Neurons)

A target cell was contacted with a patch-clamp electrode. After establishing a whole-cell configuration the intracellular potential of the cell was monitored. Application of the appropriate electroporation signal to the corresponding microelectrode induced an intracellular voltage transient up to 0 mV (the cell potential is negative, around −70 mV). The transient, due to the formation of electroporation pores and the consequent electrical communication with the grounded external electrolyte, was slowly decreasing and the cell completely recovering to the resting potential within 1-2 minutes. This was likely the time required for pores resealing. Pores formation was also demonstrated by permeation of fluorescein (a small fluorescent dye) from the external electrolyte into the cell.

Electroporation performed with the apparatus according to the present invention, and suitable electroporation signals, could be repeated during the whole patch-clamp recording session (typically 20-30 min) without any electrophysiological sign of cell damage.

As expected, the amplitude of the intracellular voltage transient induced by electroporation and the time of recovery to the resting potential were varying depending on the electroporation signal applied.

The results herein described demonstrate that the apparatus and the method according to the present invention permit an efficient individual electroporation of different kinds of cells with a variety of compounds thus fulfilling the purposes of the present invention. Further implementation or adaptations as well as embodiments readily apparent to those skilled in the art are to be considered within the scope of the present invention.

What is claimed is:

1. A biochip comprising:
 a single planar array of individually driven exclusively current/voltage delivery microelectrodes, each adapted for connection to a single cell, wherein the location of the array of microelectrodes comprises an array region comprised on an insulating layer mounted on a solid semiconductor substrate;
 means for electrically connecting said microelectrodes to a switching system, wherein each microelectrode is selectively driven by the switching system through a waveform signal with a programmed shape and timing;
 a cell culture chamber where cells can be grown and adhere in contact with said array of microelectrodes on a surface formed by said insulating layer containing said array of microelectrodes on said solid substrate; and,
 two ground reference electrodes integrated in the semiconductor substrate covered with the insulating layer, wherein the ground reference electrodes are in a planar orientation with the array of microelectrodes, and wherein the ground reference electrodes are positioned outside the array region.

2. The biochip according to claim 1 comprising a semiconductor substrate as the solid substrate covered with an insulating layer comprising said array of individually driven microelectrodes of a size comparable to the cell to be electroporated, and mounting a cell culture chamber with an opening mounted, in turn, on a support made of dielectric material, said microelectrodes being electrically connected via conductive traces to conductive pads electrically connected, in turn, to a pair of external parallel connectors through wire bonding covered by an outer portion of the cell culture chamber encircling the opening, being said cell culture chamber with the opening mounted over the top of said semiconductor substrate covered with the insulating layer, both attached on the dielectric support.

3. A biochip according to claim 2 wherein the semiconductor substrate covered with the insulating layer is a silicon substrate covered with an insulating layer preferentially of $SiO_2$.

4. The biochip according to claim 2 wherein the solid substrate is transparent.

5. The biochip according to claim 2 wherein the dielectric support is vetronite, glass or ceramic.

6. The biochip according to claim 2 wherein the microelectrodes of the array have a size with a surface of at least ten percent of the total cell membrane and preferably a diameter ranging from 1 μm to 50 μm.

7. The biochip according to claim 1 wherein the microelectrodes are of conductive or capacitive type.

8. The biochip according to claim 7 comprising conductive microelectrodes obtained over a silicon substrate covered with an insulating layer preferentially of $SiO_2$, said microelectrodes having connecting traces wherein said microelectrodes and their connecting traces being made by a "sandwich" of two titanium nitride, TiN, layers and an aluminium layer, covered with a gold layer on their active surface.

9. The biochip according to claim 7 wherein said microelectrodes are realized using Metal Oxide Semiconductor, MOS, technology.

10. The biochip according to claim 9 comprising a silicon p-type substrate in which two n-doped regions, a drain and a source, are implanted with conventional microelectronic techniques, the microelectrodes further comprising a gate, wherein the gate of these electrodes is n+ doped polysilicon and common to all devices in a row or word line, the drain of all devices in a column being connected together by using a metal contact plug and a metal line, the source of the resulting transistor being connected via a metal, usually tungsten, plug to a gold layer which acts as the active electrode.

11. The biochip according to claim 7 wherein the microelectrodes consist of a capacitive microelectrode obtained with an insulating substrate, a metal and a thin insulating layer said microelectrodes being separated by insulating material and covered in non exposed areas by a passivation layer.

12. The biochip according to claim 1 wherein the microelectrodes consist of a capacitive microelectrode obtained with an insulating substrate, a metal and a thin insulating layer, said microelectrodes being separated by insulating material and covered in non-exposed areas by a passivation layer.

* * * * *